(12) United States Patent
Harding et al.

(10) Patent No.: US 10,478,609 B2
(45) Date of Patent: *Nov. 19, 2019

(54) BLOOD CONTROL CATHETER VALVE EMPLOYING ACTUATOR WITH FLEXIBLE RETENTION ARMS

(71) Applicant: Becton, Dickinson and Company, Franklin Lakes, NJ (US)

(72) Inventors: Weston F. Harding, Lehi, UT (US); S. Ray Isaacson, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 178 days.

This patent is subject to a terminal disclaimer.

(21) Appl. No.: 15/413,211

(22) Filed: Jan. 23, 2017

(65) Prior Publication Data

US 2017/0128712 A1   May 11, 2017

Related U.S. Application Data (63) Continuation of application No. 13/954,538, filed on Jul. 30, 2013, now Pat. No. 9,592,367.

(51) Int. Cl.
*A61M 39/22* (2006.01)
*A61M 25/06* (2006.01)
(Continued)

(52) U.S. Cl.
CPC ...... *A61M 39/221* (2013.01); *A61M 25/0606* (2013.01); *A61M 39/0606* (2013.01);
(Continued)

(58) Field of Classification Search
CPC .......... A61M 25/0097; A61M 25/0606; A61M 25/0625; A61M 25/0075; A61M 39/04;
(Continued)

(56) References Cited

U.S. PATENT DOCUMENTS

| 4,616,768 A | 10/1986 | Flier |
| 4,917,668 A | 4/1990 | Haindl |
| 5,062,836 A | 11/1991 | Wendell |
| 5,250,033 A | 10/1993 | Evans et al. |

(Continued)

FOREIGN PATENT DOCUMENTS

| EP | 875262 | 11/1998 |
| EP | 1240916 | 9/2002 |

(Continued)

*Primary Examiner* — Kevin C Sirmons
*Assistant Examiner* — Leah J Swanson
(74) *Attorney, Agent, or Firm* — Kirton & McConkie; Craig Metcalf; Kevin Stinger (57) ABSTRACT

The present invention extends to a blood control catheter valve for use in a catheter adapter. The blood control catheter value employs an actuator for bypassing a septum to open the blood control catheter valve. The actuator includes flexible retention arms positioned on one end which retract into the body of the actuator while the end of the actuator passes through the septum, and then expand outwardly to maintain the actuator positioned within the septum. This design facilitates the manufacturing of catheter adapters (as well as blood control catheter valves and other components that attach to the catheter adapter) because the design can reduce the tolerance requirements of such components. Further, the design provides a reliable blood control catheter valve that does not require the catheter adapter to be increased in size to accommodate the valve.

16 Claims, 4 Drawing Sheets (51) Int. Cl.
*A61M 39/06* (2006.01)
*A61M 39/10* (2006.01)

(52) U.S. Cl.
CPC ........ *A61M 39/0693* (2013.01); *A61M 39/10* (2013.01); *A61M 2039/062* (2013.01); *A61M 2039/0653* (2013.01); *A61M 2039/1072* (2013.01); *A61M 2039/1077* (2013.01)

(58) Field of Classification Search
CPC ............ A61M 39/0693; A61M 39/045; A61M 39/0606; A61M 39/221; A61M 2039/062; A61M 2039/0633; A61M 2039/064; A61M 2039/0646; A61M 2039/066; A61M 2039/0666; A61M 2039/0673; A61M 2039/1072; A61M 2039/1077
See application file for complete search history.

(56) References Cited

U.S. PATENT DOCUMENTS

| | | |
|---|---|---|
| 7,507,222 B2 | 3/2009 | Cindrich et al. |
| 2007/0083157 A1 | 4/2007 | Belley et al. |
| 2007/0083162 A1 | 4/2007 | O'Reagan |
| 2008/0097386 A1 | 4/2008 | Osypka |
| 2008/0300538 A1 | 12/2008 | Schweikert et al. |
| 2009/0143739 A1 | 6/2009 | Nardeo et al. |
| 2009/0234290 A1 | 9/2009 | Fisher et al. |
| 2009/0259175 A1 | 10/2009 | Nordgren |
| 2010/0204648 A1 | 8/2010 | Stout et al. |
| 2011/0046570 A1 | 2/2011 | Stout et al. |

FOREIGN PATENT DOCUMENTS

| | | |
|---|---|---|
| WO | 93/11696 | 6/1993 |
| WO | 98/00195 | 1/1998 |
| WO | 2006/059540 | 6/2006 |
| WO | 2010/093791 | 8/2010 |
| WO | 2012/009028 | 1/2012 |
| WO | 2012/083245 | 6/2012 |
| WO | 2013/052746 | 4/2013 |

BLOOD CONTROL CATHETER VALVE EMPLOYING ACTUATOR WITH FLEXIBLE RETENTION ARMS

RELATED APPLICATION

This application is a continuation of U.S. patent application Ser. No. 13/954,538, entitled BLOOD CONTROL CATHETER VALVE EMPLOYING ACTUATOR WITH FLEXIBLE RETENTION ARMS, filed on Jul. 30, 2013, which is incorporated herein in its entirety.

BACKGROUND OF THE INVENTION

The present invention relates generally to catheters, such as intravenous ("IV") catheters, and more particularly to blood control valves for use in catheters.

Catheters are widely used throughout the medical community for a wide range of procedures and treatments. Catheters are commonly used for a variety of infusion therapies. Catheters are used for infusing fluid, such as normal saline solution, various medicaments, and total parenteral nutrition, into a patient, withdrawing blood from a patient, or monitoring various parameters of the patient's vascular system.

A common type of IV catheter is an over-the-needle peripheral IV catheter. As its name implies, an over-the-needle catheter is mounted over an introducer needle having a sharp distal tip. At least the distal portion of the catheter tightly engages the outer surface of the needle to prevent peelback of the catheter and thus facilitate insertion of the catheter into the blood vessel. The catheter and the introducer needle are assembled so that the distal tip of the introducer needle extends beyond the distal tip of the catheter with the bevel of the needle facing up away from the patient's skin. The catheter and introducer needle are generally inserted at a shallow angle through the patient's skin into a blood vessel.

The process of placing a catheter requires careful balance and control over the catheter. Typically an IV catheter will be incorporated into a catheter assembly. The catheter assembly may include various components to aid in the use and placement of the IV catheter. Typically a catheter assembly will provide a gripping surface to aid in griping and controlling the IV catheter during insertion. The gripping surface will commonly provide opposing surfaces whereby a user may grasp and hold the device during insertion.

Figure 1:
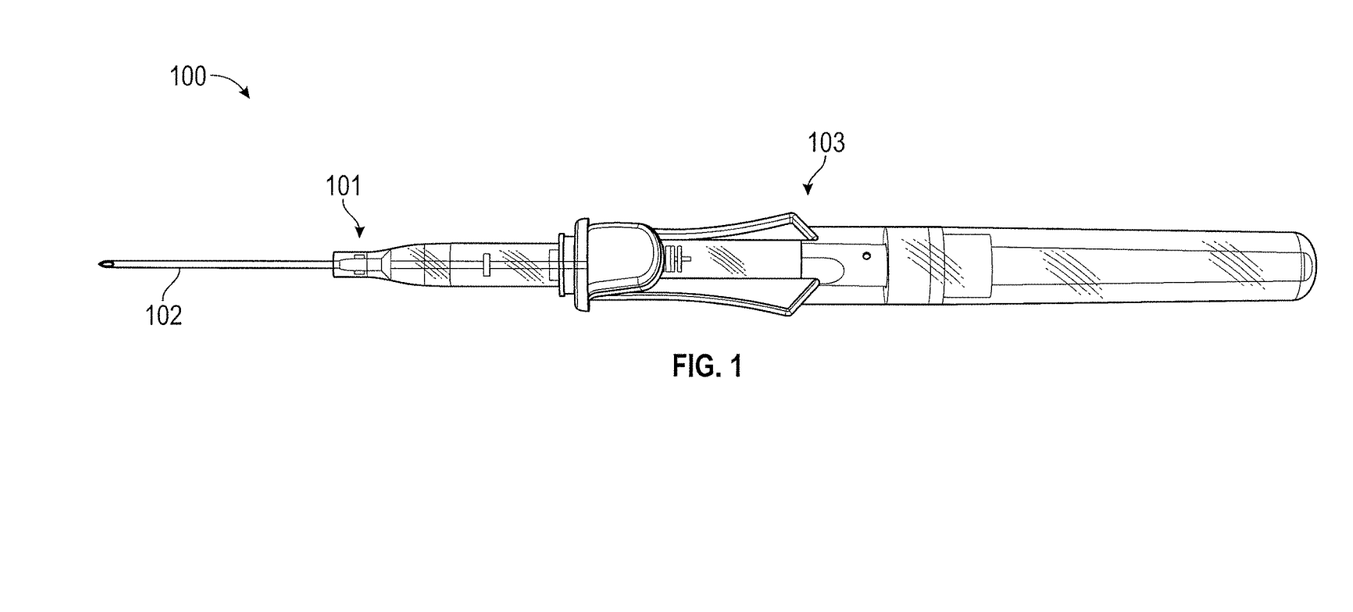
FIG. 1 illustrates an example of a common IV catheter that includes a catheter adapter, a needle, and a needle shield.

FIG. 1 illustrates an example of a common IV catheter 100. Catheter 100 includes a catheter adapter 101 and a needle shield 103. A needle 102 is initially contained within a catheter extending out from catheter adapter 101. In some current IV catheters, catheter adapter 101 includes a septum through which needle 102 extends. The septum maintains a seal around needle 102 while the needle is inserted into the patient's vasculature so that blood cannot escape through catheter adapter 101 where it may come in contact with the external environment.

Once the catheter is placed inside the patient's vasculature, needle 102 can be withdrawn from catheter adapter 101 into needle shield 103. Once needle 102 is withdrawn, the septum can reseal to prevent blood from flowing out of catheter adapter 101 until another device (which usually has a male luer connector) is attached to the catheter adapter and separates the septum to allow fluid flow to or from the other device.

In some IV catheters, the catheter adapter includes an actuator that is forced through the septum when another device is attached to the catheter adapter. In other words, after the needle has been removed from the catheter adapter, the septum is again opened when a connector of the other device forces the actuator through the septum.

One problem that exists with current IV catheters that employ an actuator is that the actuator must be designed to remain within the catheter on the proximal side of the septum until activation (e.g. until the other device forces the actuator through the septum). Some designs of actuators for use in catheter adapters employ relatively small fixed arms that extend laterally from the actuator and snap into a small groove in the internal wall of the catheter adapter. To accommodate this design, the actuator and catheter adapter must be manufactured with tight tolerances. The tight tolerances are required to ensure that the fixed arms will fit into the grooves. Manufacturing these components with tight tolerances is oftentimes undesirable. For example, the cost or difficultly of manufacturing these components with tight tolerances may be burdensome or impractical in many cases.

Another problem with such designs is that the actuator, once forced through the septum, is only held in place by the friction between the septum and the nose of the actuator. In other words, the actuator is only held within the septum by the force that the septum applies around the actuator. No other structure is provided to ensure that the actuator does not slip back out from within the septum. Because of this, it is possible that the actuator may be disengaged from the septum which can inhibit the flow of fluids through the catheter adapter or otherwise affect the performance of the catheter.

BRIEF SUMMARY OF THE INVENTION

The present invention extends to a blood control catheter valve for use in a catheter adapter. The blood control catheter value employs an actuator for bypassing a septum to open the blood control catheter valve. The actuator includes flexible retention arms positioned on one end which retract into the body of the actuator while the end of the actuator passes through the septum, and then expand outwardly to maintain the actuator positioned within the septum.

This design facilitates the manufacturing of catheter adapters (as well as blood control catheter valves and other components that attach to the catheter adapter) because the design can reduce the tolerance requirements of such components. In other words, because the design employs flexible retention arms, the tolerance between the catheter adapter and the actuator is less important than when fixed retention arms are employed (i.e. because the flexible retention arms can flex to account for variances in the distance between the internal wall of the catheter adapter and the actuator). Further, the design provides a reliable blood control catheter valve that does not require the catheter adapter to be increased in size to accommodate the valve.

In a first embodiment, the present invention is implemented as a blood control catheter valve for use in a catheter adapter. The blood control catheter valve comprises a septum configured to be retained within a catheter adapter, and an actuator configured to pass partially through the septum to open the blood control catheter valve. The actuator includes one or more flexible retention arms that are biased in an outward position. The one or more flexible retention arms fold inwardly as the actuator passes through the septum and return to the outward position after the one or more flexible retention arms have passed through the septum thereby retaining the actuator within the septum.

In some embodiments, prior to the actuator passing partially through the septum, the one or more flexible retention arms are biased outwardly into one or more recesses formed in an internal wall of the catheter adapter thereby retaining the actuator within the catheter adapter.

In some embodiments, the actuator is forced partially through the septum when a device is connected to the catheter adapter.

In some embodiments, the device has a male luer connector that inserts into the catheter adapter to force the actuator partially through the septum as the device is connected to the catheter adapter.

In some embodiments, the actuator includes one or more channels formed in an exterior surface of the actuator. The one or more channels are configured to receive the one or more flexible retention arms when the one or more flexible retention arms are folded inwardly.

In some embodiments, the one or more channels have a depth such that when the one or more flexible retention arms are folded into the one or more channels, an exterior surface of the one or more flexible retention arms is flush with an exterior surface of the actuator.

In some embodiments, the actuator has a length that is less than a first length of the catheter adapter. The first length is the length between a proximal end of the catheter adapter and the position of the septum within the catheter adapter.

In some embodiments, the actuator includes an internal channel that extends through the length of the actuator. The internal channel forms a path for fluid flow through the actuator.

In some embodiments, the one or more flexible retention arms comprise two flexible retention arms formed on opposite sides of the actuator.

In some embodiments, the actuator includes one or more protrusions at a proximal end of the actuator. The one or more protrusions form a surface against which a device forces when the device is inserted into the catheter adapter.

In some embodiments, the catheter adapter is an intravenous catheter adapter.

In a second embodiment, the present invention is implemented as an intravenous catheter assembly comprising a catheter adapter, a septum contained within the catheter adapter, and an actuator configured to pass partially through the septum to enable fluid flow through the catheter adapter. The actuator includes one or more flexible retention arms that are biased in an outward position. The one or more flexible retention arms fold inwardly as the actuator passes through the septum and return to the outward position after the one or more flexible retention arms have passed through the septum thereby retaining the actuator within the septum.

In some embodiments, the intravenous catheter assembly includes a needle contained within the catheter adapter, the needle passing through the actuator and the septum.

In some embodiments, the intravenous catheter assembly includes a needle shield attached to the catheter adapter, the needle shield configured to retain the needle after the needle is retracted from the catheter adapter.

In some embodiments, the septum is configured to reseal after the needle is retracted from the catheter adapter thereby preventing fluid flow through the catheter adapter until the actuator passes partially through the septum.

In some embodiments, prior to the actuator passing partially through the septum, the one or more flexible retention arms are biased outwardly into one or more recesses formed in an internal wall of the catheter adapter thereby retaining the actuator within the catheter adapter.

In some embodiments, the actuator is forced partially through the septum when a device is connected to the catheter adapter.

In some embodiments, the device has a male luer connector that inserts into the catheter adapter to force the actuator partially through the septum as the device is connected to the catheter adapter.

In some embodiments, the actuator includes one or more channels formed in an exterior surface of the actuator. The one or more channels are configured to receive the one or more flexible retention arms when the one or more flexible retention arms are folded inwardly.

In a third embodiment, the present invention is implemented as a catheter adapter having a blood control catheter valve. The blood control catheter valve comprises a septum positioned within the catheter adapter, and an actuator configured to pass partially through the septum to open the blood control catheter valve. The actuator includes one or more flexible retention arms that are biased in an outward position. The one or more flexible retention arms fold inwardly as the actuator passes through the septum and return to the outward position after the one or more flexible retention arms have passed through the septum thereby retaining the actuator within the septum. Prior to the actuator passing partially through the septum, the one or more flexible retention arms are biased outwardly into one or more recesses formed in an internal wall of the catheter adapter thereby retaining the actuator within the catheter adapter.

This summary is provided to introduce a selection of concepts in a simplified form that are further described below in the Detailed Description. This Summary is not intended to identify key features or essential features of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

The present invention extends to a blood control catheter valve for use in a catheter adapter. The blood control catheter value employs an actuator for bypassing a septum to open the blood control catheter valve. The actuator includes flexible retention arms positioned on one end which retract into the body of the actuator while the end of the actuator passes through the septum, and then expand outwardly to maintain the actuator positioned within the septum.

This design facilitates the manufacturing of catheter adapters (as well as blood control catheter valves and other components that attach to the catheter adapter) because the design can reduce the tolerance requirements of such components. In other words, because the design employs flexible retention arms, the tolerance between the catheter adapter and the actuator is less important than when fixed retention arms are employed (i.e. because the flexible retention arms can flex to account for variances in the distance between the internal wall of the catheter adapter and the actuator). Further, the design provides a reliable blood control catheter valve that does not require the catheter adapter to be increased in size to accommodate the valve.

In a first embodiment, the present invention is implemented as a blood control catheter valve for use in a catheter adapter. The blood control catheter valve comprises a septum configured to be retained within a catheter adapter, and an actuator configured to pass partially through the septum to open the blood control catheter valve. The actuator includes one or more flexible retention arms that are biased in an outward position. The one or more flexible retention arms fold inwardly as the actuator passes through the septum and return to the outward position after the one or more flexible retention arms have passed through the septum thereby retaining the actuator within the septum.

In a second embodiment, the present invention is implemented as an intravenous catheter assembly comprising a catheter adapter, a septum contained within the catheter adapter, and an actuator configured to pass partially through the septum to enable fluid flow through the catheter adapter. The actuator includes one or more flexible retention arms that are biased in an outward position. The one or more flexible retention arms fold inwardly as the actuator passes through the septum and return to the outward position after the one or more flexible retention arms have passed through the septum thereby retaining the actuator within the septum.

In a third embodiment, the present invention is implemented as a catheter adapter having a blood control catheter valve. The blood control catheter valve comprises a septum positioned within the catheter adapter, and an actuator configured to pass partially through the septum to open the blood control catheter valve. The actuator includes one or more flexible retention arms that are biased in an outward position. The one or more flexible retention arms fold inwardly as the actuator passes through the septum and return to the outward position after the one or more flexible retention arms have passed through the septum thereby retaining the actuator within the septum. Prior to the actuator passing partially through the septum, the one or more flexible retention arms are biased outwardly into one or more recesses formed in an internal wall of the catheter adapter thereby retaining the actuator within the catheter adapter.

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 2:
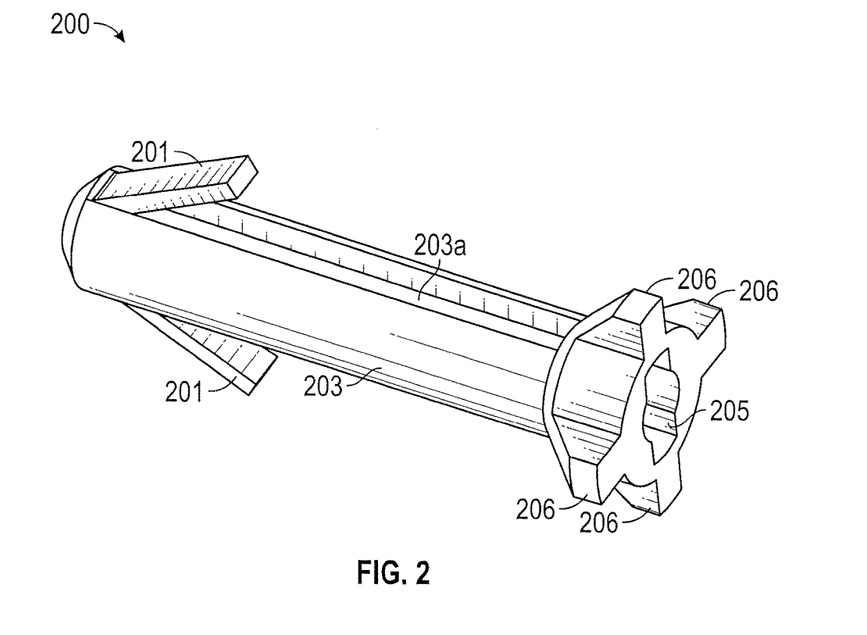
FIG. 2 illustrates an example of an actuator that can be used within a blood control catheter valve in accordance with one or more embodiments of the invention.

FIG. 2 illustrates an example of an actuator 200 that can be used within a blood control catheter valve in accordance with one or more embodiments of the invention. The design of actuator 200 is an example of how the present invention facilitates the manufacturing of catheter adapters (as well as blood control catheter valves and other components that attach to the catheter adapter). This example design can reduce the tolerance requirements of such components by employing flexible retention arms which minimize the importance of the tolerance between the catheter adapter and the actuator.

Actuator 200 includes a body 203 through which a channel 205 is formed. Channel 205 allows a needle to be inserted through actuator 200 and also allows fluid to flow through actuator 200 once the blood control catheter valve is open. Actuator can be formed of any suitable material. In many cases, actuator 200 can be formed of a material that provides a degree of flexibility as will be further described below.

Body 203 also includes channels 203a (only one of which is shown in FIG. 2) and flexible retention arms 201 which are biased outwardly and configured to fold down into channels 203a. Because flexible retention arms 201 can fold into channels 203a, the overall diameter of the portion of actuator 200 that passes through a septum is not increased (i.e. arms 201 can fold into channels 203a so that the outer surface of arms 201 are flush with the outer surface of body 203). In some cases, arms 201 can be flexible due to the material from which actuator 200 is made. For example, plastic based material can be used so that arms 201 can be molded from the same material as the remainder of actuator 200 while still retaining a degree of flexibility to provide the benefits described below.

Other materials can also be used. For example, certain metals can provide an appropriate degree of flexibility to allow actuator 200 to be formed as a single piece. Also, it is feasible that arms 201 can be formed as separate components that are attached to the body of actuator 200 in some manner that allows arms 201 to remain flexible although this approach is often not preferred due to the increased difficulty of manufacturing an actuator in this manner.

Actuator 200 can also include protrusions 206 which extend radially from body 203. Protrusions 206 can provide a greater surface area against which another component (e.g. a male luer) can push to force actuator 200 through a septum as will be further described below. Protrusions 206 can also assist in aligning actuator 200 within the catheter adapter.

Figure 3A:
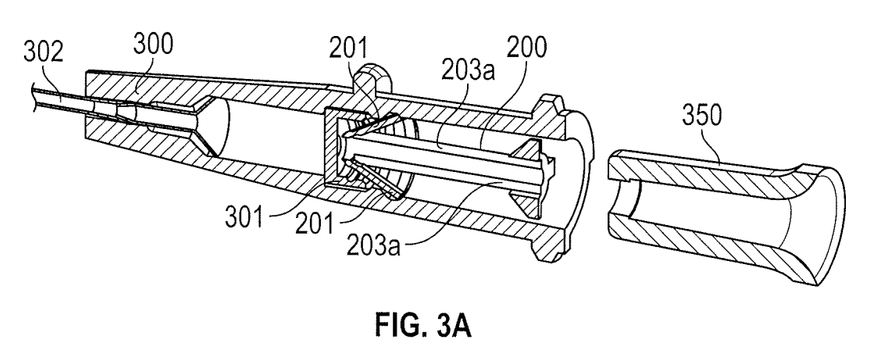
FIGS. 3A-3C illustrate a cross-sectional perspective view of a catheter adapter to demonstrate how the actuator of FIG. 2 is used to open the blood control catheter valve.
Figure 3B:
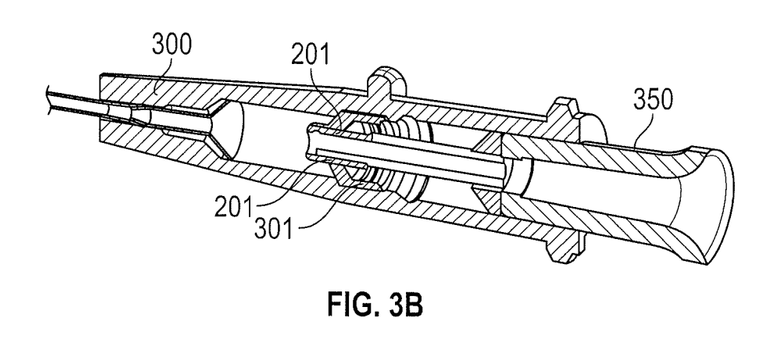
Figure 3C:
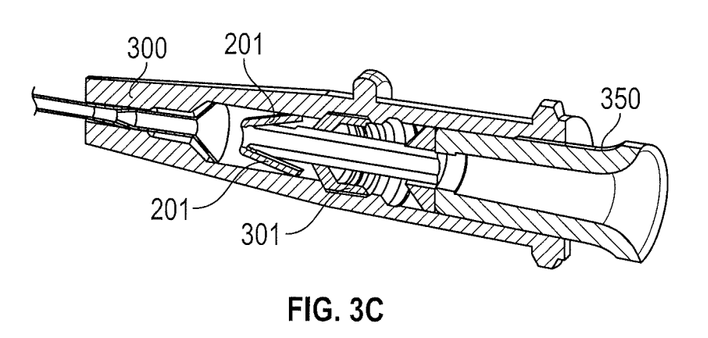

FIGS. 3A-3C illustrate a cross-sectional perspective view of a catheter adapter 300 that includes a blood control catheter valve consisting of actuator 200 and septum 301, and male luer 350. Catheter adapter 300 can be similar to catheter adapter 101 shown in FIG. 1 or similar to many other types of catheter adapters. In other words, the blood control catheter valve of the present invention can be used in virtually any catheter adapter. Catheter adapter 300 includes a catheter 302 that can be inserted into the vasculature of a patient. Septum 301 is positioned within the interior of catheter adapter 300. In many cases, catheter adapter 300 is supplied initially with a needle (e.g. as shown in FIG. 1) that passes through septum 301 and catheter 302 and is used to insert catheter 302 into the patient's vasculature.

FIG. 3A illustrates the state of catheter adapter 300 before male luer 350 has been connected. Catheter adapter 300 can be in this state after catheter 302 has been inserted into the vasculature of a patient (e.g. after a needle has been withdrawn from catheter adapter 300), but prior to another component being connected to catheter adapter 300. In this state, actuator 200 is positioned to the proximal side of septum 301. Septum 301 is therefore closed in this state thereby preventing blood from flowing from the patient's vasculature out through catheter adapter 300.

FIG. 3B illustrates the state of catheter adapter 300 while male luer 350 is being forced into catheter adapter 300. As shown, actuator 200 is configured such that male luer 350 forces actuator 200 through septum 301 (which may include a small slit) as male luer 350 is advanced into catheter adapter 300. When actuator 200 is forced through septum 301, arms 201 fold towards body 203 and into channels 203a. In this way, actuator 200 can easily be forced through septum 301. At this point, channel 205 of actuator 200 allows fluids to flow from (e.g. blood) or into (e.g. medications) catheter 302.

FIG. 3C illustrates the state of catheter adapter 300 after male luer 350 has been fully inserted into catheter adapter 300. As shown, actuator 200 has been forced sufficiently through septum 301 that arms 201 have sprung back to an outward position. In this position, arms 201 prevent actuator 200 from passing back through septum 301.

Figure 4A:
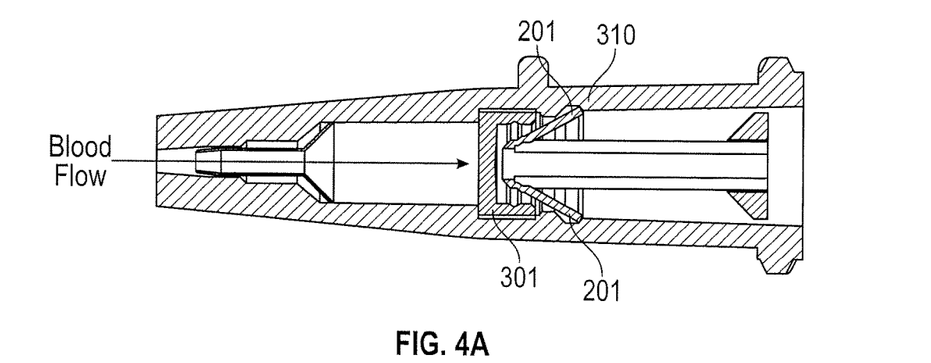
FIGS. 4A-4C illustrate a cross-sectional side view of the catheter adapter shown in FIGS. 3A-3C.
Figure 4B:
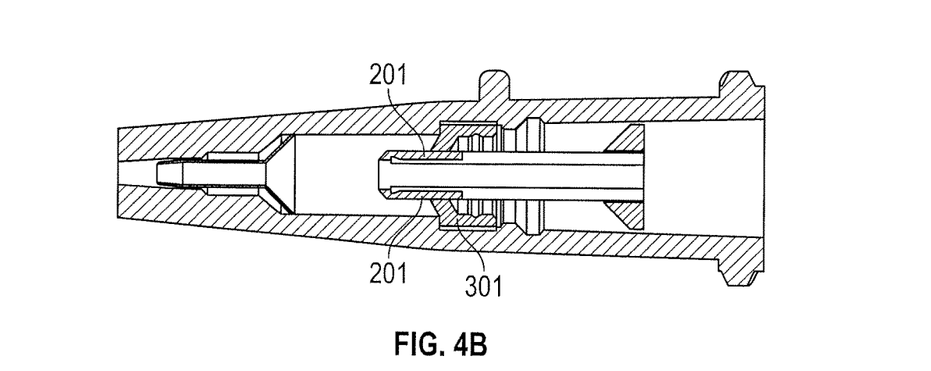
Figure 4C:
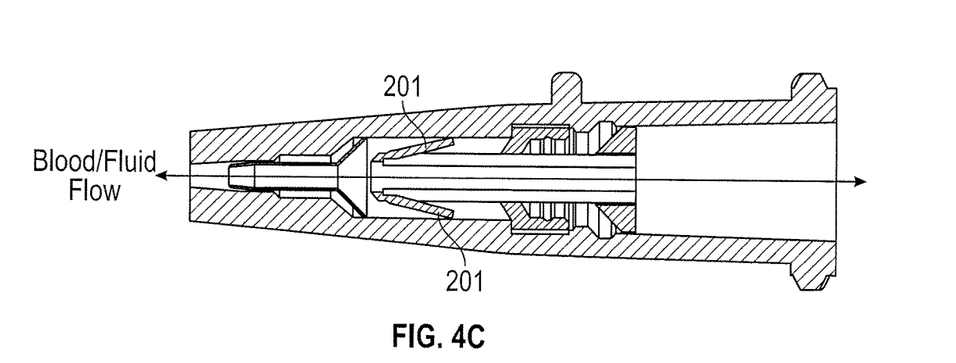

FIG. 4A-4C illustrate a cross-sectional side view of the catheter adapter shown in FIGS. 3A-3C. FIG. 4A illustrates recess 310 that can be formed in catheter adapter 300. Arms 201 extend into recess 310 prior to activation of the valve thereby preventing actuator 200 from falling out of catheter adapter 300. FIG. 4A also shows that, prior to activation, blood can flow into catheter adapter 300 up to septum 301 which blocks the blood flow from passing out through the other end of catheter adapter 300. In this way, after catheter 302 is inserted into a patient's vasculature, the clinician need not worry about blood flowing out through catheter adapter 300 before another device is attached to open the blood control catheter valve.

FIG. 4B illustrates the position of actuator 200 while actuator 200 is being advanced through septum 301 (male luer 350 is not shown). As shown, arms 201 are folded down into channels 203a allowing actuator 200 to easily pass through septum 301.

FIG. 4C illustrates the position of actuator 200 after actuator 200 has been forced through septum 301 sufficiently to allow arms 201 to expand outwardly. In this position, arms 201 block actuator 200 from returning back through septum 301.

The design of actuator 200 provides various benefits. For example, a catheter adapter with a blood control valve generally must be sufficiently long to accommodate the length of the male luer connector and to accommodate the components of the valve as well as any movement required by the components to open the valve. Actuator 200 can be sized to be initially secured entirely within the catheter adapter on the proximal side of the septum (e.g. the right side as shown in FIG. 4A).

This reduced length is also beneficial because it minimizes the required length of the catheter adapter on the distal side of the septum (e.g. the left side in FIG. 4C). In other words, the catheter adapter must have sufficient length on the distal side of the septum to allow actuator 200 to advance sufficiently for the male luer to be fully inserted into the catheter adapter. This distance required to fully inset the male luer is oftentimes not consistent from device to device. Accordingly, the use of arms 201 facilitate the securing of actuator 200 within the septum even when actuator 200 is not advanced the same distance.

For example, in FIG. 4C, actuator 200 is shown as having been advanced so that arms 201 are positioned substantially distally from the septum (i.e. there is a gap between the septum and the arms). However, arms 201 can still provide the same securing function even when actuator 200 is advanced a shorter distance than shown in FIG. 4C (e.g. when actuator 200 is advanced just enough to allow arms 201 to expand after passing through the septum). This flexibility makes actuator 200 more reliable given the variations in catheter adapter and male luer lengths.

The design of actuator 200 also provides the benefit of reducing the tolerances required for the diameters of the actuator and the catheter adapter. For example, because arms 201 are biased outwardly, variations in the internal diameter of the catheter adapter (or more specifically, the internal diameter of recess 310) do not affect the ability of arms 201 to secure actuator 200 within the catheter adapter prior to activation. This outward bias of arms 201 also allows arms 201 to secure actuator 200 within the septum regardless of the internal diameter or shape of the catheter adapter.

In short, the design of actuator 200 allows blood control catheter valves to be manufactured with much looser tolerances than required by many current designs. By loosening the tolerance requirements, actuator 200 makes the blood control catheter valve of the present invention easier to manufacture and more reliable even with the variations in size of common catheter adapters and male luer connectors.

Although the above description has used the example of a male luer connector, the blood control catheter valve of the present invention can also be configured to work with another type of connector that inserts into the catheter adapter. Also, the blood control catheter valve can be used within many different types of catheter adapters, and can be part of a prepackaged IV catheter assembly that includes a needle and needle shield (e.g. similar to catheter 100 shown in FIG. 1). In such cases, the needle can initially pass through channel 205 while actuator 200 is positioned as shown in FIG. 4A.

Further, although actuator 200 has been described as including two arms 201, an actuator in accordance with the present invention can equally have one or more arms 201 while still providing the desired functions. Also, although actuator 200 has been described as including channels 203a, actuator 200 can also be configured without channels 203a. In such cases, arms 201 can fold down against an exterior wall of body 203 while actuator 200 passes through septum 301. However, it is generally preferable to include a channel 203a for each arm 201 to facilitate the forcing of actuator 200 through septum 301.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A catheter assembly comprising:
   a catheter adapter;
   a septum configured to be retained within the catheter adapter; and
   an actuator configured to pass partially through the septum to open the septum, wherein the actuator comprises a plurality of proximally-facing flexible retention arms that are biased in an outward position, the actuator further comprising a plurality of channels disposed in an outer surface of the actuator, wherein the flexible retention arms fold inwardly into the plurality of channels and are flush with the outer surface as the actuator moves distally through the septum and return to the outward position after the flexible retention arms have moved distally through the septum thereby retaining the actuator within the septum.

2. The catheter assembly of claim 1, wherein, prior to the actuator passing partially through the septum, the flexible retention arms are biased outwardly into one or more recesses formed in an internal wall of the catheter adapter thereby retaining the actuator within the catheter adapter.

3. The catheter assembly of claim 1, wherein the actuator is configured to pass partially through the septum to open the septum when a separate device is inserted distally into the catheter adapter, wherein the separate device has a male luer connector that inserts into the catheter adapter to contact and force the actuator partially through the septum as the separate device is connected to the catheter adapter.

4. The catheter assembly of claim 1, wherein the actuator has a length that is less than a first length of the catheter adapter, the first length being the length between a proximal end of the catheter adapter and the position of the septum within the catheter adapter.

5. The catheter assembly of claim 1, wherein the flexible retention arms comprise two flexible retention arms formed on opposite sides of the actuator.

6. The catheter assembly of claim 1, wherein the catheter adapter is an intravenous catheter adapter.

7. An intravenous catheter assembly comprising:
   a catheter adapter;
   a septum contained within the catheter adapter; and
   an actuator configured to pass partially through the septum to open the septum, wherein the actuator comprises a plurality of channels formed in an exterior surface of the actuator, wherein the actuator further comprises a plurality of flexible retention arms biased in an outward position, wherein the plurality of channels are configured to receive the flexible retention arms when the flexible retention arms are folded inwardly.

8. The catheter assembly of claim 7, wherein the actuator further comprises an internal channel that extends through a length of the actuator, the internal channel forming a path for fluid flow through the actuator.

9. The catheter assembly of claim 8, further comprising:
   a needle contained within the catheter adapter, the needle passing through the internal channel of the actuator and through the septum.

10. The catheter assembly of claim 7, further comprising:
    a needle shield attached to the catheter adapter, the needle shield configured to retain a needle after the needle is retracted from the catheter adapter.

11. The catheter assembly of claim 7, wherein the septum is configured to reseal after a needle is retracted from the catheter adapter thereby preventing fluid flow through the catheter adapter until the actuator passes partially through the septum.

12. The catheter assembly of claim 7, wherein, prior to the actuator passing partially through the septum, the flexible retention arms are biased outwardly into one or more recesses formed in an internal wall of the catheter adapter thereby retaining the actuator within the catheter adapter.

13. The catheter assembly of claim 7, wherein a separate device has a male luer connector that inserts into the catheter adapter to contact and force the actuator partially through the septum as the separate device is connected to the catheter adapter.

14. A catheter assembly comprising:
    a catheter adapter;
    a septum configured to be retained within the catheter adapter; and
    an actuator positioned entirely within the catheter adapter and configured to pass partially through the septum to open the septum, the actuator comprising a proximally-facing flexible retention arm biased in an outward position and foldable inwardly, wherein the actuator comprises an internal channel that extends through a length of the actuator, the internal channel forming a path for fluid flow through the actuator, wherein in response to the actuator passing partially through the septum such that the proximally-facing flexible retention arm is disposed on a distal side of the septum and a proximal end of the actuator is disposed on a proximal side of the septum, the actuator is retained within the septum by the flexible retention arm disposed in the outward position.

15. The catheter assembly of claim 14, wherein a proximal end of the actuator comprises multiple protrusions extending radially from a body of the actuator, wherein the actuator passes partially through the septum in response to another component contacting the multiple protrusions.

16. The catheter assembly of claim 14, wherein the actuator further comprises multiple flexible retention arms, wherein in response to the actuator passing partially through the septum, the actuator is retained within the septum by the flexible retention arms.

* * * * *